(12) United States Patent
Al-Eid et al.

(10) Patent No.: US 8,522,600 B2
(45) Date of Patent: Sep. 3, 2013

(54) FLUID COMPOSITIONAL ANALYSIS BY COMBINED GAS CHROMATOGRAPHIC AND DIRECT FLASH METHODS

(75) Inventors: Mohammad Ibrahim Al-Eid, Saihat (SA); Emmanuel C. Uba, Saudi Aramco (SA); Mohammed Sajjad Ali, Thoqbah-Khobar (SA)

(73) Assignee: Saudi Arabian Oil Company (SA)

( * ) Notice: Subject to any disclaimer, the term of this patent is extended or adjusted under 35 U.S.C. 154(b) by 470 days.

(21) Appl. No.: 12/902,495

(22) Filed: Oct. 12, 2010

(65) Prior Publication Data

US 2012/0085149 A1   Apr. 12, 2012

(51) Int. Cl.
*G01N 30/04* (2006.01)

(52) U.S. Cl.
USPC ........................................................ 73/23.38

(58) Field of Classification Search
USPC .................. 73/23.35, 23.38, 23.41; 210/656, 210/767, 774
See application file for complete search history.

(56) References Cited

U.S. PATENT DOCUMENTS

| | | | | |
|---|---|---|---|---|
| 2,386,334 | A * | 10/1945 | Morris ........................... | 585/849 |
| 2,913,397 | A * | 11/1959 | Murray, Jr. et al. ............ | 208/107 |
| 3,467,615 | A * | 9/1969 | McConnell et al. ........... | 523/455 |
| 3,751,966 | A * | 8/1973 | Ryan et al. .................... | 73/23.36 |
| 4,159,894 | A | 7/1979 | Hu | |
| 4,459,142 | A | 7/1984 | Goddin, Jr. | |
| 4,559,063 | A | 12/1985 | Munari et al. | |
| 5,099,743 | A | 3/1992 | Rounbehler et al. | |
| 5,191,211 | A | 3/1993 | Gorman, Jr. | |
| 5,268,302 | A | 12/1993 | Rounbehler et al. | |
| 5,310,681 | A | 5/1994 | Rounbehler et al. | |
| 5,508,204 | A | 4/1996 | Norman | |
| 5,611,846 | A | 3/1997 | Overton et al. | |
| 5,719,323 | A | 2/1998 | Ellzy | |
| 6,187,581 | B1 * | 2/2001 | Sicotte et al. ................. | 435/262 |
| 6,237,396 | B1 | 5/2001 | Durand et al. | |
| 6,776,025 | B2 | 8/2004 | Lechner-Fish | |
| 6,968,729 | B1 * | 11/2005 | Karlsson et al. ............. | 73/23.41 |
| 7,081,615 | B2 | 7/2006 | Betancourt et al. | |
| 7,373,285 | B2 * | 5/2008 | Webb .............................. | 703/2 |
| 7,467,540 | B2 | 12/2008 | Kriel | |
| 2005/0257600 | A1 * | 11/2005 | Karlsson et al. ............. | 73/23.41 |
| 2006/0021940 | A1 | 2/2006 | Bertoncini et al. | |
| 2008/0141767 | A1 | 6/2008 | Raghuraman et al. | |

(Continued)

FOREIGN PATENT DOCUMENTS

WO    2010042794  A2    4/2010

OTHER PUBLICATIONS

Petroff et al., "Automated Simulated Distillation by Gas Chromatography Performance Test for Petroleum Product Control," 1987, Journal of Chromatography, 395, pp. 241-254.*

(Continued)

*Primary Examiner* — John Fitzgerald
(74) *Attorney, Agent, or Firm* — Bracewell & Giuliani LLP

(57) ABSTRACT

A method and apparatus for providing compositional analysis of hydrocarbon fluids from well samples up to a C30+ fraction. The method includes the steps of heating a sample to a temperature of about 220° F., and collecting the liquid and gaseous fractions therefrom. Both the liquid and gaseous fractions are analyzed by gas chromatography. Additionally, the volume of the gas, and the volume, molecular weight and mass of the liquid are determined. The results are then analyzed to provide a total composition of the hydrocarbon fluids.

14 Claims, 5 Drawing Sheets

(56) References Cited

U.S. PATENT DOCUMENTS

| | | |
|---|---|---|
| 2008/0295607 A1 | 12/2008 | Di Maggio et al. |
| 2009/0192768 A1 | 7/2009 | Zuo et al. |
| 2012/0197053 A1* | 8/2012 | Cantrell et al. ............... 585/251 |

OTHER PUBLICATIONS

Supelco, "Separation of Hydrocarbons by Packed Column GC," 1995, Sigma-Aldrich Co., Bulletin 743L.*

Durand et al., "Simulated Distillation Methods for Petroleum Fractions with Minimal Residue in the Boiling Range of 35-700C," Sep. 1998, Journal of Chromatographic Science, vol. 36, pp. 431-434.*

Durand et al., "Improvement of Simulated Distillation Methods by Gas Chromatography in Routine Analysis," 1999, Oil & Gas Science and Technology-Rev. IFP, vol. 54, No. 4, pp. 431-438.*

Kriel et al., "Improved Gas Chromatographic Analysis of Reservoir Gas and Condensate Samples", SPE Int'l Symposium on Oilfield Chemistry (Mar. 1, 1989), pp. 397-411.

PCT Notification of Transmittal of the International Search Report and the Written Opinion of the International Searching Authority, or the Declaration; dated Aug. 1, 2012; International Application No. PCT/US2011/055599; International File Date: Oct. 10, 2011.

* cited by examiner

FLUID COMPOSITIONAL ANALYSIS BY COMBINED GAS CHROMATOGRAPHIC AND DIRECT FLASH METHODS

FIELD OF THE INVENTION

This invention relates to a method for obtaining compositional analysis of hydrocarbons present in a geological formation. More specifically, the invention relates to an improved method for obtaining extended hydrocarbon fluid compositional analysis of a well sample, up to and including a C30+ fraction, by direct flash method and gas chromatography.

BACKGROUND OF THE INVENTION

Analyses of the hydrocarbon fluids from a reservoir are usually carried out by direct distillation of the sample, followed by gas chromatographic analysis of one or more distilled fractions. One major weakness of this technique, however, is that current techniques for this process typically do not produce extended compositional data (i.e., up to and including a $C_{30+}$ fraction) that are necessary for use with modern compositional and process simulations. Instead, current techniques generally only provide data for the C12+ fraction, and possibly the C20+ fractions.

Hydrocarbon or petroleum reservoir fluids exist in formations as "live fluids." Because the fluid is at elevated pressure and temperature conditions within the formation, non-hydrocarbon gases (e.g., $N_2$, $CO_2$, $H_2S$) and light hydrocarbons (e.g., $C_1$ to $C_5$) are typically dissolved in the oil. During production, as fluid containing the hydrocarbons flows to the wellhead and subsequently to the surface separators, the gases and light hydrocarbons dissolved therein begin to evolve due to lower pressures and temperatures. The evolved gases thus can alter the composition of the original oil, as it existed in the formation, and two phases, a liquid phase and a vapor phase, emanate. A surface separator separates the liquid and vapor phases. Vapor is collected at the separator gas orifice and liquid at the separator oil outlet. These separate liquid and vapor streams are then analyzed in a laboratory to obtain their individual molecular compositions. The prior art techniques take the individual molecular compositions, and then mathematically recombine them using the original gas-oil ratio to produce a total well-stream composition, which typically includes the individual values of each of the hydrocarbon components up to a C12+ fraction. (That is, individual hydrocarbons are reported up to and including the C11 fraction, and a C12+ fraction is also reported). In a similar manner, a bottom-hole sample is flashed at ambient conditions to produce a flashed vapor, and the flashed vapor and remaining liquid are then each separately analyzed for their molecular compositions. Each of these compositions are mathematically recombined with the volumes of vapor and liquid recovered to produce the well stream composition, usually to C12+.

One prior art apparatus and method for compositional analyses utilizes a topping unit, a distillation column, and at least one gas chromatograph. The topping unit includes interconnected calibrated aluminum cylinders, with each cylinder being connected to a manometer with tubing and valves. The whole unit is enclosed with an insulated material and cabinet doors. The distillation system consists of a distillation flask, e.g. a 500 mL distillation flask, having a tapered joint, an inlet to charge the sample, and a thermometer to measure the still temperature. A heating mantle and a thermocouple are included for measuring the temperature of the fluid in the flask. It includes a low temperature distillation apparatus where the flashed oil is heated to about 608° F. and the vapor can be condensed in a condenser supplied with a circulation of cold water to leaving a liquid C12+ fraction residue. Evolved gas can be collected in the evacuated topping unit and the condensate cut fraction collected in a receiver. Both the gas and the condensate fractions may be analyzed by gas chromatography, and the density and molecular weight of the residual oil C12+ fraction measured and used to calculate the total fluid composition. This method suffers, however, in that it only provides compositional data up to the C12+ fraction.

Thus, there exists a need to provide methods of analyzing hydrocarbon fractions up to at least a C20+ fraction, preferably up to a C30+ fraction for use in advanced simulations.

SUMMARY

The current invention provides methods for the rapid and accurate determination of the composition of a hydrocarbon sample, such as a hydrocarbon reservoir sample, wherein the composition includes hydrocarbon components up to and including a C30+ fraction.

In one aspect, a method for separating and analyzing a hydrocarbon sample is provided. The method includes the steps of separating the hydrocarbon sample into a first fraction and a second fraction, wherein the first fraction includes hydrocarbons having a boiling point less than about 220° F. and the second fraction includes hydrocarbons having a boiling point greater than about 220° F. The method further includes the step of measuring the volume of the first fraction, and the steps of measuring the mass, density and molecular weight of the second fraction. The method includes the step of determining the composition of the first fraction by gas chromatography with a first gas chromatograph, determining the composition of the second fraction by gas chromatography with a second gas chromatograph, and combining the compositions of the first and second fractions to obtain a total composition of the hydrocarbon sample up to a C30+ hydrocarbon fraction.

In another aspect, the present invention provides a method for analyzing the hydrocarbon composition of a hydrocarbon bearing reservoir. The method includes the steps of obtaining a hydrocarbon sample from the hydrocarbon bearing reservoir, and heating the hydrocarbon sample to produce two fractions. The first fraction has an upper boiling point less than or equal to the lower boiling point of the second fraction. The method includes the step of providing the first and second fractions to first and second gas chromatographs to obtain compositional analysis of the first and second fractions; and combining the compositional analysis of the first fraction and the compositional analysis of the second fraction to obtain a total compositional analysis of the hydrocarbon sample.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein are set forth without any loss of generality, and without imposing limitations, relating to the claimed invention.

Whereas many of the prior art techniques for calculating total compositional analysis of hydrocarbons, including cryogenic distillation, fractional distillation and direct sampling techniques, are time consuming, complicated and have certain inaccuracies associated with the results, techniques are needed that improve upon these shortcomings. Additionally, current industry standards only provide fractional analysis of hydrocarbon fractions up to a C7+ or C12+ fraction, which is insufficient for many of the simulation programs being used today to evaluate reservoirs. Thus, the present invention addresses problems associated with prior art techniques by providing methods for analyzing hydrocarbon fractions that are accurate, rapid, less complicated, and involve minimal human error.

Figure 1:
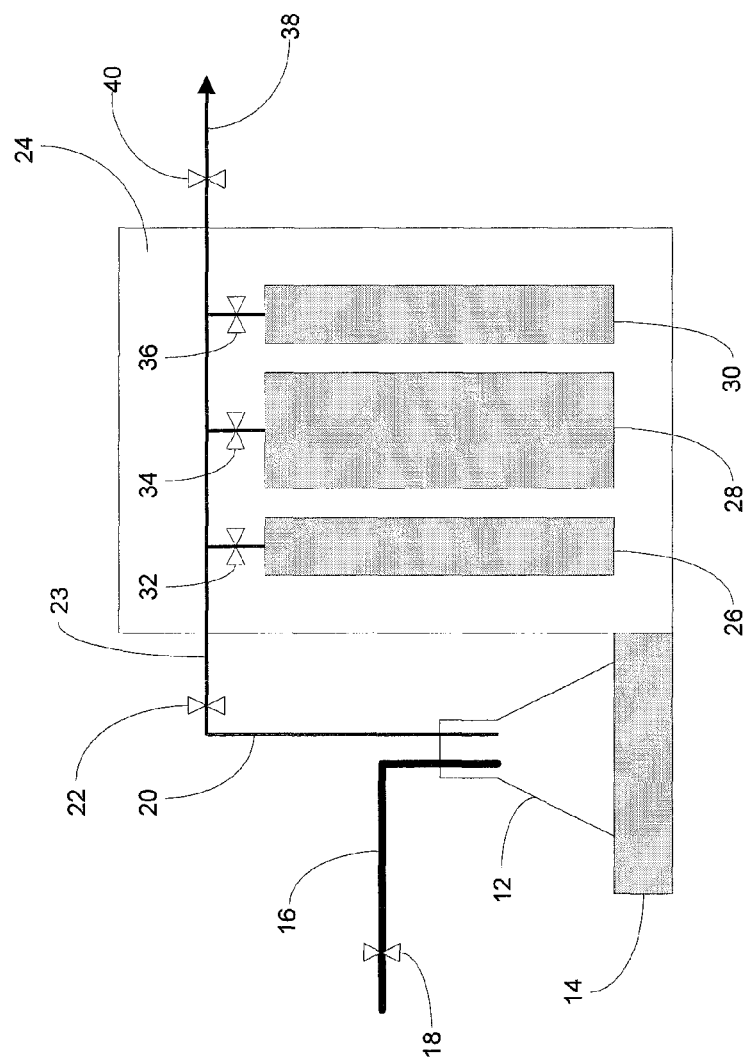
FIG. 1 provides an apparatus for the compositional analysis of a hydrocarbon liquid according to one embodiment of the present invention.

FIG. 1 shows apparatus 10 for separating and analyzing reservoir fluids to provide compositional analysis according to one embodiment of the present invention. Flask 12 is provided and is heated by heating plate 14 or a like heating device (e.g., heating mantel, heating tape, and like devices). Flask 12 includes stirring means for homogenizing samples while being heated, such as a mechanical stirrer or a magnetic stir plate and magnet. Flask 12 can be sized according to the desired sample size. Hydrocarbon containing fluids can be supplied to flask 12 via line 16, and flow of the fluids to the flask can be controlled with valve 18. Hydrocarbon and other gases produced by the heating of the fluid in flask 12 exit the flask via outlet line 20 to topping unit 24. The flow of gases from flask 12 to topping unit 24 can be controlled with valve 22. Topping unit 24 can include multiple vessels for collecting flashed gas. For example, in an embodiment of the invention, topping unit 24 can include three vessels; first vessel 26, second vessel 28, and third vessel 30, wherein the first, second, and third vessels are connected to topping unit inlet line 23 by first valve 32, second valve 34, and third valve 36, respectively. Flow of gas from flask 12 via outlet line 20 to topping unit inlet line 23 can be controlled with valve 22. Topping unit 24 gas outlet 38 can be controlled by valve 40. Gas outlet 38 can be used to supply a gas sample to an associated gas chromatograph. Apparatus 10 further includes at least one gas chromatograph for analyzing samples. In certain embodiments, apparatus 10 can include at least two gas chromatographs, wherein the first gas chromatograph is used for analysis of a gas fraction and a second gas chromatograph is used for analysis of a liquid fraction.

Hydrocarbon liquid samples are heated in flask 12 to a temperature of between approximately 200° F. and 220° F., alternatively between about 200° F. and 210° F., alternatively between about 210° F. and 220° F., alternatively approximately 220° F. to evaporate the lighter ends up to about hydrocarbons including C6. In certain embodiments, the temperature to which the hydrocarbon liquid samples in flask 12 are heated is between about 200° F. and 250° F., alternatively between about 210° F. and 230° F. The residual liquid in flask 12, having a boiling point greater than about 200° F., or in certain embodiments, having a boiling point greater than about 220° F., and the topped gas are separately collected and stored, and can each separately be connected to a gas chromatograph for subsequent analysis. In certain embodiments, the residual liquid and gas fractions are separately analyzed by gas chromatography.

In certain embodiments, one or more vessels within topping unit 24 can have a larger volume than the other vessels. For example, as shown in FIG. 1, second vessel 28 can have a larger volume than first vessel 26 and third vessel 30. In one embodiment of the present invention, first and third vessels, 26 and 30, respectively, can have an internal volume of between about 4 and 5 L, and second vessel 28 can have a volume of between about 15 and 25 L.

In addition, apparatus 10 can include means for measuring the density, volume and/or molecular weight of the residual liquid fraction. Apparatus 10 can also includes means for measuring volume and/or density of the gas fraction. Exemplary apparatuses for the measurement of density and molecular weight include the Anton Paar DMA 450 Densitometer and the Cryette WR, respectively. The cylinders for topping unit 24 can each be pre-calibrated such that Cylinder 1 has a known and pre-determined volume, for example Cylinder 1 can have a volume of 4.578 L, Cylinder 2 can have a volume of 19.32 L, and Cylinder 3 can have a volume of 4.578 L. All volume calibrations are conducted at 760 mmHG and a temperature of 180° F. The density of the gas can be determined, for example, with a gas chromatograph.

Apparatus 10 can also include a computing device (not shown) selected from one or more networked personal computer, laptop computer, server, or like device. The computing device can include one or more software correlation module installed on said computing device, or accessible to said computer device, for performing various calculations including correlations, corrections, or statistical methods, and for storing data relating to correlations, corrections, or statistical methods. The computing device can include computer instruction code, such as for example, Java, C, C++, Visual Basic, and the like. The software code can be stored as a series of instructions or commands on a readable computer medium, including random access memory, read only memory, a magnetic medium, such as for example, a hard drive or floppy disc, an optical medium, or like device. In addition, the computing device can include software operable to receive and store values corresponding to measurements relating to the volume of the gas and liquid fractions, the mass of the liquid fraction, the molecular weight of the liquid fraction, and the composition of the gas and liquid fractions, as determined by a gas chromatograph, and to provide results related to the total composition of a wellbore samples.

The computing device can include a computer program product, wherein the computer program product that is provided can include a set of instructions that, when executed by the computer, cause the computer to perform various operations, including receiving physical measurements of and relating to the gas and liquid residue fractions, receiving gas chromatograph composition data for and relating to the gas and liquid residue fractions, calculating the compositional data for the gas and liquid fractions, combining the compositional data for the gas and liquid residue fractions to produce a total compositional analysis for a hydrocarbon sample, correlating the density, mass and volume measurements for the gas and liquid residue fractions to determine mole concentration and molecular weight, and correlating the density, mass, volume, and molecular weights with the gas chromatograph compositional data.

In certain embodiments, the computer program product can be configured to mathematically recombine the gas and the liquid compositions, as determined by gas chromatography, and to further provide either a well-stream composition or a separator liquid composition. The calculated molecular weight and density of a hydrocarbon sample using an estimated value for the C30+ fraction can be provided to the computing device, and a computer program included therein can then correlate and compare the gas and liquid compositions of the hydrocarbon sample, as determined by gas chromatography, to the measured molecular weight and density of the hydrocarbon sample. After the determination of the C30+ fraction and an initial confirmatory match has been made, the properties of additional plus fractions, such as the C7+, C12+, and/or C20+ fraction, can then be determined and calculated. This technique can be used to acquire extended fluid composition up to the $C_{30+}$ fraction, along with other plus fraction average properties.

In certain embodiments, the gas analysis gas chromatograph apparatus and the liquid residue gas chromatograph apparatus can be separately configured. For example, in certain embodiments, the gas analysis gas chromatograph can include various columns for the separation of various components contained in the gas sample, including low molecular weight hydrocarbons. For example, the gas chromatograph can include a molecular sieve for separation of oxygen, nitrogen and methane gases. In certain embodiments, the column can include a 60/80 mesh, which may have dimensions of 15' by 125" OD. In certain preferred embodiments, the 60/80 mesh column can be positioned outside of the oven of the gas chromatograph, to increase elution of various components as it has been found that certain compounds elute better at or about room temperature.

Other suitable columns for use in the gas analysis gas chromatograph can include an HP HeySep Q 60/80 mesh column, for example having a length of about 8 feet and an OD of about 125", to separate carbon dioxide, ethane, propane, and hydrogen sulfide compounds from the gas fraction; a 35% DC 200/500 on chromosorb PAW-DMCS 80/100, for example having a length of about 15 feet and an OD of about 125", for back-flushing heavy components, such as hydrocarbons having a greater mass than about heptane, or the like; and/or an HP-1 cross linked methyl silicone capillary column, for example having a length of about 50 meters, for separation of hydrocarbons having between about 1 and 10 carbon atoms.

The dual channel high sensitivity thermal conductivity detector and a flame ionization detectors of the gas analyzer can be configured as follows. In certain embodiments, the thermal conductivity detector can be positioned as the front detector and can have a maximum temperature of up to about 200° C., and a reference flow of up to about 40 mL/min. The flame ionization detector can be positioned as the back detector and can be configured to have a maximum temperature of about 250° C. and a hydrogen/air flow ratio of between about 1:20 and 1:5, alternatively between about 1:12 and 1:8, or preferably the hydrogen/air flow ratio is about 1:10.

The condensate and residue gas chromatograph can include an Ultra-Alloy-1 (MS/HT) column, preferably including Valco Series W-Model FU0041 injection valves, which can be connected to a flame ionization detector. Typically, the flame ionization detector can be operated at temperatures of up to about 350° C., having a hydrogen/air flow ratio of between about 1:20 and 1:5, alternatively between about 1:12 and 1:8, or preferably the hydrogen/air flow ratio is about 1:10, utilizing a carrier gas, such as helium, which can be supplied at a carrier gas flow rate of about 25 mL/min.

Injection of either the gas or liquid residue hydrocarbon sample into a gas chromatograph can include a step of establishing a carrier gas flow in the gas chromatograph through the chromatographic columns, wherein the carrier gas is heated to a temperature sufficient to vaporize volatile hydrocarbon components and any hydrocarbon solvent, such that the hydrocarbon components and solvent pass through the chromatographic column with the carrier gas.

Apparatus 10 can include multiple calibrated aluminum cylinders, for example three calibrated aluminum cylinders, which can be connected to each other, wherein each can also be connected to a manometer (not shown) with tubing and valves. The manometer(s) can be configured to measure the pressure within the cylinder(s), both before and after evacuation, and after gas sampling, to provide initial and final system pressures. The specific cylinder(s) are selected for use in the present invention on a sample by sample basis, based upon certain sample properties, including the gas-to-oil ratio (GOR) and the bubble point pressure of the hydrocarbon sample.

A still can be directly connected to the inlet of the topping unit. Heating means, such as a heating mantle, hot plate, heating tape, or like means can be provided to heat fluid contained in the still. Means for measuring the temperature of liquids within the still, such as a thermometer, thermocouple, or like means, can also be provided.

Figure 2:
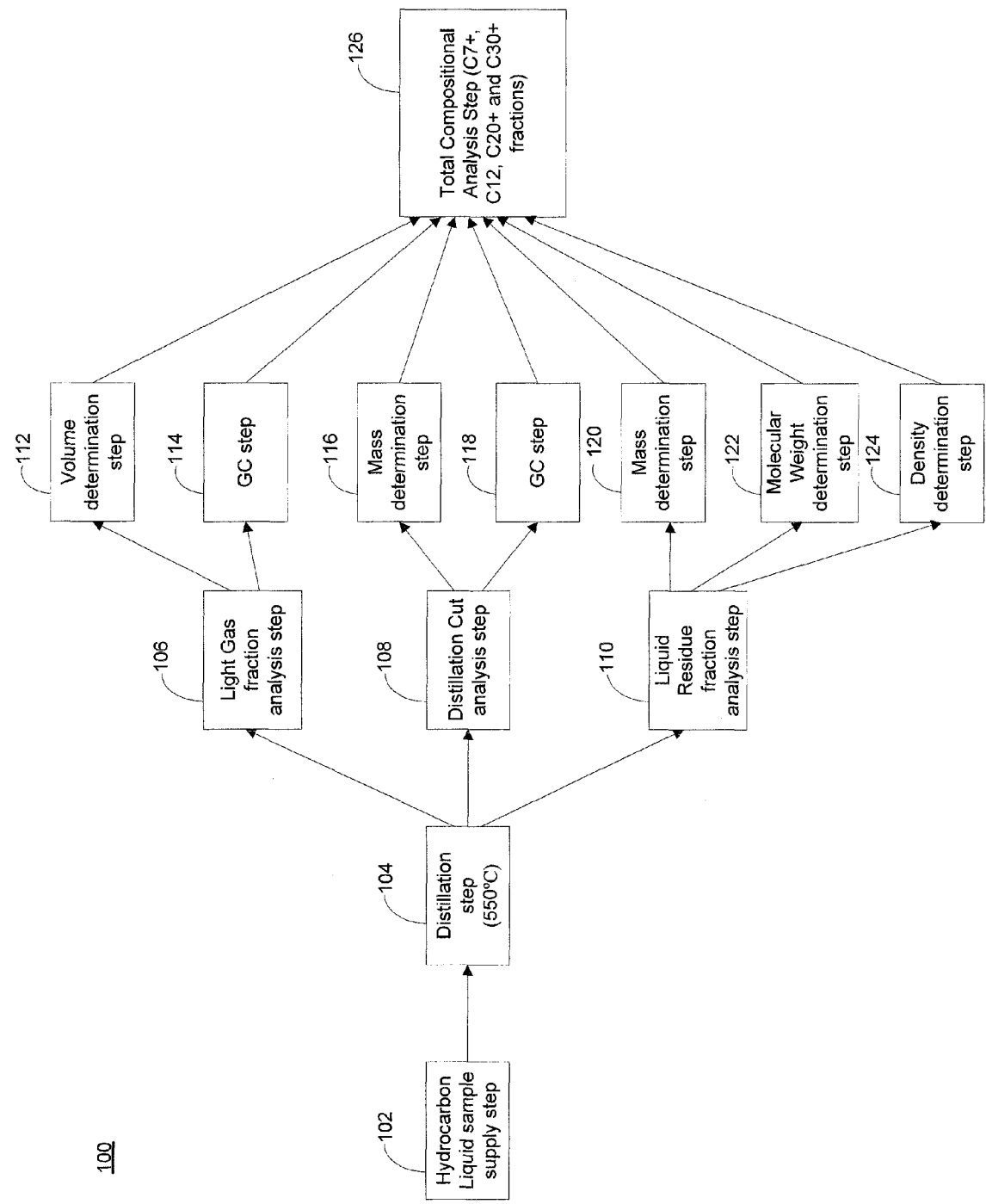
FIG. 2 provides a method for the compositional analysis of a hydrocarbon liquid according to one embodiment of the present invention.

As shown in FIG. 2, method 100 for determining the total compositional analysis of a hydrocarbon sample is provided. In first supply step 102, a hydrocarbon containing liquid is supplied to distillation step 104, where the hydrocarbon containing liquid sample is heated to a temperature of at least about 530 F, alternatively at least about 550° F., to produce three fractions; a light gas fraction, a distillation cut, and a liquid residue fraction. Distillation step 104 utilizes cold water circulation through a condenser or like means to recover the hydrocarbons. Evolved gas is collected in a topping unit, and gas condensate is collected in a receiver. Light gas fraction analysis step 106 analyzes a light gas fraction that includes hydrocarbons up to about hexanes (i.e., having up to about 6 carbon atoms), or hydrocarbons having a boiling point of less than about 69° C. The light gas fraction can also include light non-hydrocarbon gases, such as hydrogen sulfide and nitrogen. Distillation cut analysis step 108 analyzes a fraction that includes hydrocarbons having between about 6 and 11 carbon atoms, or hydrocarbons having a boiling point between about 69° C. and 200° C. Liquid residue fraction analysis step 110 analyzes a fraction that includes hydrocarbons having about 12 and greater carbon atoms, or hydrocarbons having a boiling point of greater than about 200° C.

Light gas fraction analysis step 106 includes volume determination step 112, and gas chromatography step 114, wherein the gas chromatography step provides compositional analysis of the light gas fraction. Distillation cut analysis step 108 includes a mass determination step 116, and a gas chromatography step 118. Liquid residue fraction analysis step 110 includes a mass determination step 120, a molecular weight determination step 122, and a density determination step 124. The results of all determination steps for the light gas fraction, distillation cut, and liquid residue fractions are then combined and undergo further calculations in total compositional analysis step 126. The liquid residue fraction includes the C12+ fraction. Current methods of analysis do not provide compositional analysis of a hydrocarbon fraction beyond the C12+ fraction.

Figure 3:
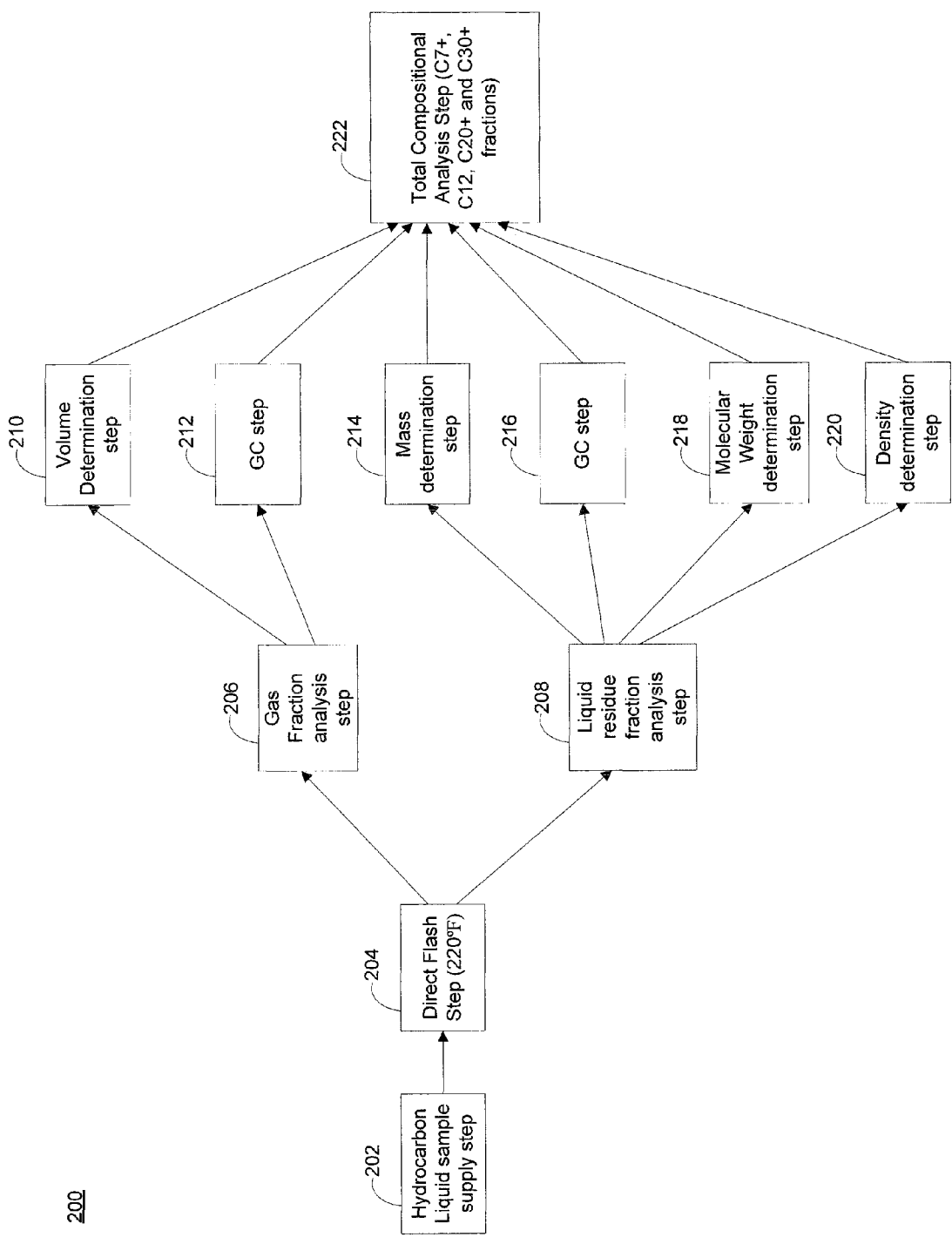
FIG. 3 provides a method for the compositional analysis of a hydrocarbon liquid according to one embodiment of the present invention.

FIG. 3 provides an improved method for determining the total composition of a hydrocarbon containing wellbore sample, according to one embodiment of the present invention, for the compositional analysis of hydrocarbon sample. In a first supply step 202, a hydrocarbon sample is supplied to a vessel, such as a flask, and flash heated to a temperature of at least about 200° F. to provide two fractions, a gas fraction, which includes hydrocarbons having up to about 8 carbon atoms, and a liquid residue fraction, having hydrocarbons having about 7 carbon atoms and greater. Gas fraction analysis step 206 includes volume determination step 210 and gas chromatography step 212, which provides compositional analysis of the gas fraction. Liquid residue fraction analysis step 208 includes mass determination step 214, molecular weight determination step 218, density determination step 220, and gas chromatography step 216, which provides compositional analysis of the liquid residue fraction. The results of all of the above described measurement steps for the gas and liquid residue fractions can then be combined, and can undergo further calculations total compositional analysis step 222.

The method provided in FIG. 3 utilizes a flash technique step 204 where the hydrocarbon sample fluids are heated under atmospheric conditions to at least about 200° F., preferably up to about 220° F., to evaporate the lighter end hydrocarbons up to about hexane or heptane (i.e., about C6 or C7, respectively). The flash technique step 204 for preparing the gas fraction and liquid residue fraction according to the present invention does not require high heat, does not require reduced pressure, does not employ a distillation process, does not require a cold water input for condensation purposes, and does not require the separate step of collecting of a light condensate fraction for analysis. The present method is simpler in both the preparation of fractions and the analysis thereof, and allows for a reduction in the time required for analysis by up to about 50%, thus doubling the number of different analyses that can be completed.

Both the gas fraction, which can include hydrocarbons up to and including about hexane and other light compounds, and the liquid residue fraction, which can include hydrocarbons including about 6 and greater carbon atoms (i.e., hexane and greater hydrocarbons), can be analyzed by gas chromatography steps, 212 and 216 respectively, to provide individual compositional analysis results for each of the two fractions. In certain embodiments, separate gas chromatographs can be utilized for the analysis, and in certain embodiments the separate gas chromatographs can be separately configured for the analysis of gas or liquid residue fractions.

Total compositional analysis step 222 can include the steps of providing all collected data, including the gas chromatography results of the gas fraction and liquid residue fraction, as well as gas fraction volume determination step 210, liquid residue fraction mass determination step 214, liquid residue fraction molecular weight determination step 218, and liquid residue fraction density determination step 220, and the step calculating the total composition make-up of the hydrocarbon sample from these measured values. The steps for the determination of the molecular weight and density are further described herein.

In preferred embodiments, the C30+ fraction of the hydrocarbon sample is first computed from the liquid residue fraction, typically by matching a pre-calculated liquid residue fraction molecular weight and density with measured liquid residue fraction molecular weight and measured liquid residue fraction density. After the C30+ fraction has been determined and matched, the other fractions, such as a C7+, C12+, and C20+ fractions can then be calculated.

Figure 4:
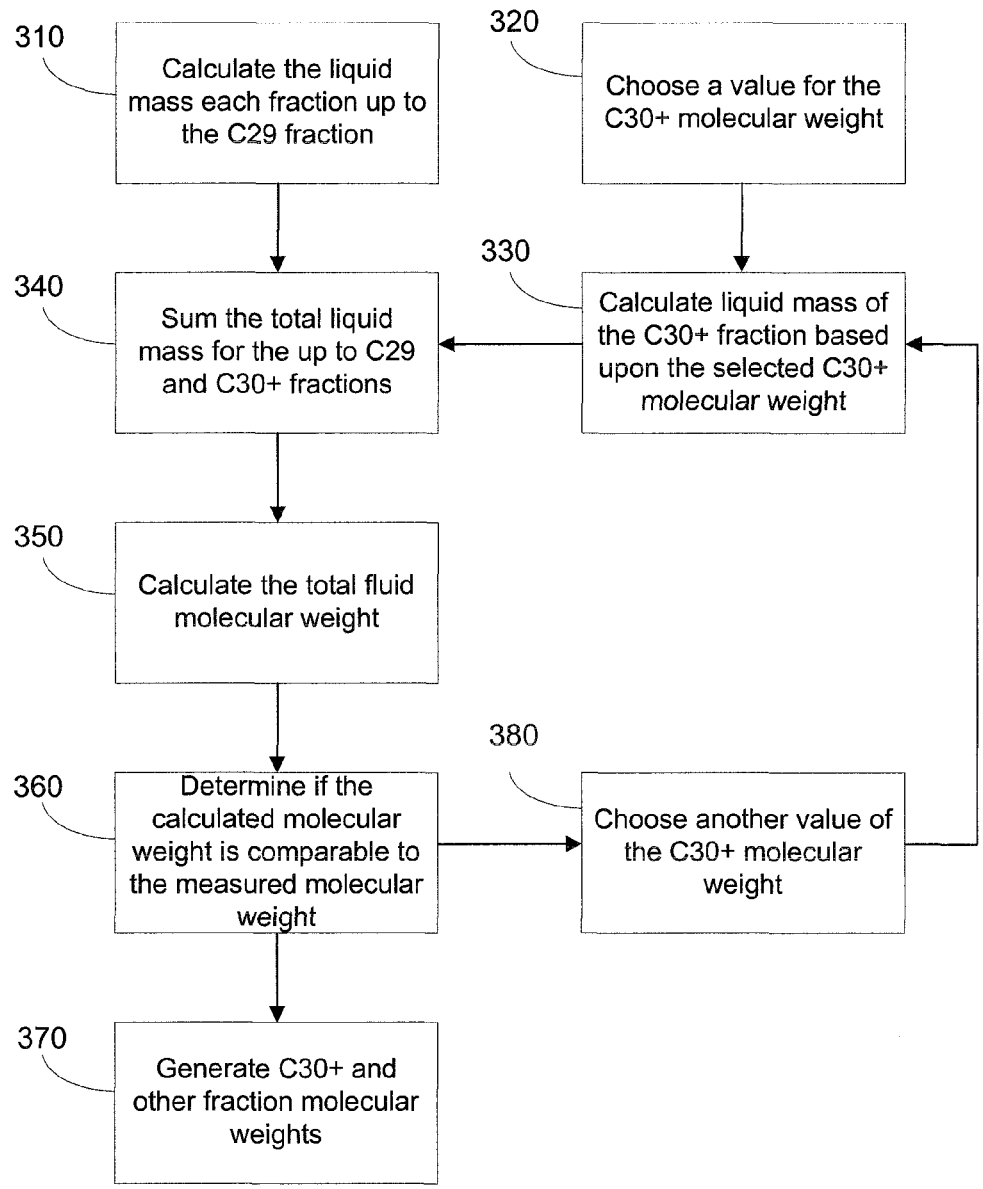
FIG. 4 provides a method for the determination of the molecular weight of a C30+ hydrocarbon fraction.

Referring now to FIG. 4, a process 300 for determining the molecular weight of a hydrocarbon sample is provided. In first step 310, the liquid masses of each component in the hydrocarbon sample, up to and including the C29 component, are calculated. A gas chromatograph can be used to determine the compositional make-up of the hydrocarbon sample up to the C29 component. For clearly defined components, such as C1 to C5, the liquid masses are calculated by multiplying the molecular weight of the component by the measured mole fraction of the component. For fractional cuts, such as for example, C6, C12, up to C29, the molecular weight is selected from published values (such as, Handbook of Natural Gas Engineering, by Donald Katz). In step 320, a value is selected for the molecular weight of the C30+ fraction. In certain embodiments, such as for condensate, an estimated value of the molecular weight of the C30+ fraction of between about 450 g/mol and about 700 g/mol is used. Alternatively, in certain embodiments, such as for black oil, an estimated value of the molecular weight of between about 550 g/mol and about 900 g/mol is used. In step 330, the liquid mass of the C30+ fraction is calculated, based upon the molecular weight of the C30+ fraction, as provided in step 320. In step 340, the liquid mass of the fractions up to the C29 component, as calculated in step 310, and the liquid mass of the C30+ fraction, as calculated in step 330, are combined to give a total liquid mass of the sample.

In step 350, the total fluid molecular weight is calculated, such as by freezing point depression utilizing a Cryette WR apparatus. In step 360, the calculated molecular weight from step 350 is compared against the measured molecular weight, to determine if the difference between the calculated molecular weight and measured molecular weight are within a pre-determined range to be considered sufficiently accurate. Typically, the values of the calculated molecular weight and the measured molecular weight are desired to be within about 10% of each other to be considered sufficiently accurate. If the values are sufficiently accurate, then in step 370, the molecular weight values for all fractions, including the C30+ fraction, are determined. Alternatively, if the values are not sufficiently accurate (that is, the difference between the calculated molecular weight and the measured molecular weight is greater than about 10%), then in step 380, another molecular weight for the C30+ fraction is selected, and step 330 for the determination of the liquid mass of the C30+ fraction is repeated using the molecular weight value selected in step 380. The procedure is repeated until the difference between the calculated molecular weight and the measured molecular weight for the fluid is determined to be sufficiently accurate.

Figure 5:
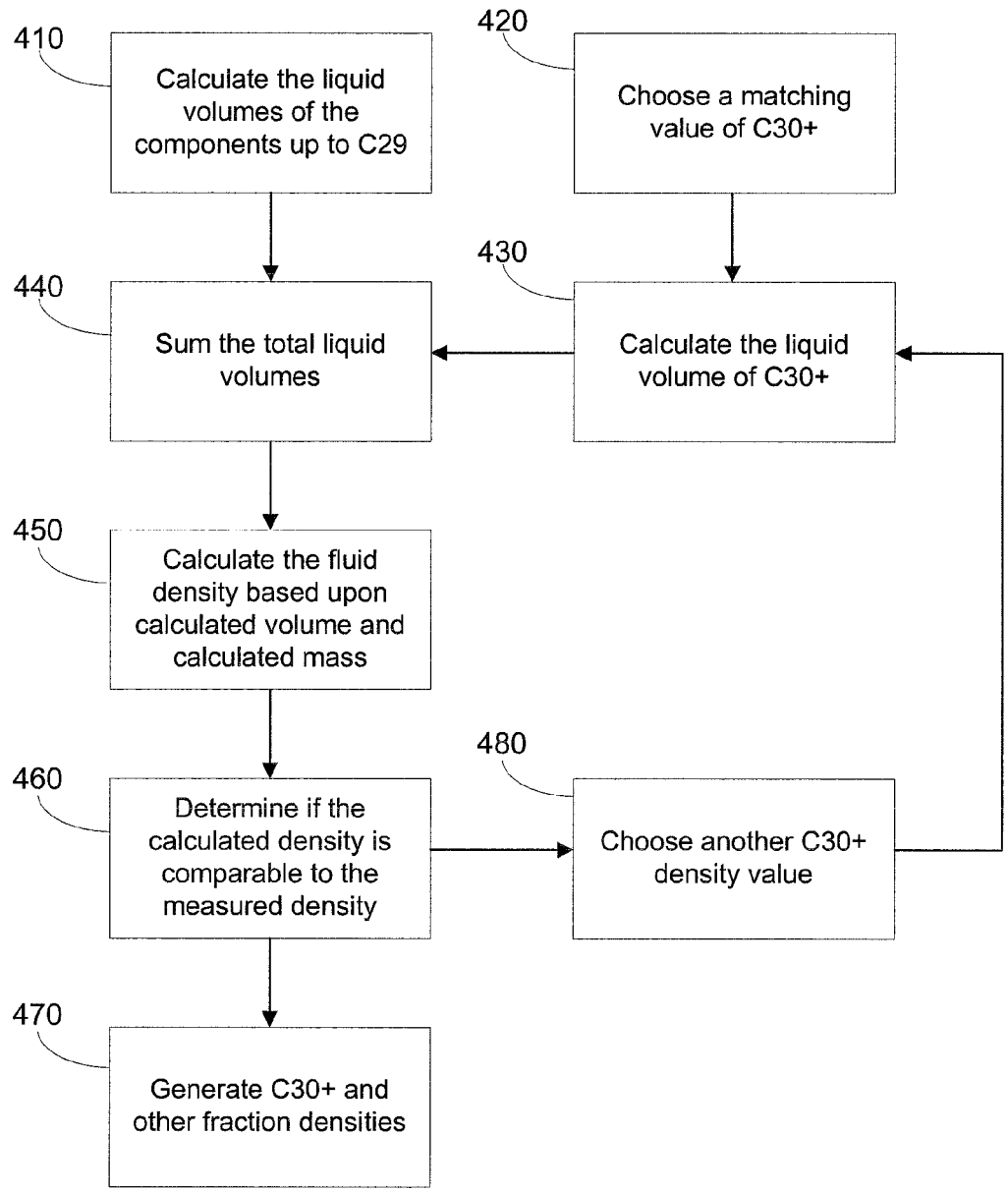
FIG. 5 provides a method for the determination of the density of a C30+ hydrocarbon fraction.

Referring now to FIG. 5, the procedure for determining the density of the C30+ fraction 400 is provided. In first step 410, the liquid volumes of the components up to the C29 component, including non hydrocarbon components like nitrogen gas, are calculated. In step 420, a value for the density of the C30+ fraction is chosen. In certain embodiments, such as for a condensate sample, a C30+ density value of between about 0.80 g/cc and about 0.90 g/cc is selected. In certain other embodiments, such as for a black oil sample, a C30+ density value of between about 0.85 g/cc and about 0.95 g/cc is selected. In step 430, the C30+ liquid volume is then calculated using the selected density of the C30+ fraction. The C30+ liquid volume is calculated by dividing the C30+ liquid weight by the selected C30+ density. In step 440, the total liquid volumes for the fractions up to the C29 component and the C30+ fractions are calculated.

In step 450, the fluid density of the total liquid sample is then calculated, such as with an Anton Paar DMA 450 Densitometer, or like device. The fluid density for the total liquid sample is calculated by dividing the total liquid weight of the sample, as determined in step 340 described above, by the total liquid volume determined in step 440. In step 460, the calculated fluid density determined in step 450 is compared with the measured fluid density to determine if the calculated density and the measured density are within a pre-determined range such that they are to be considered sufficiently accurate to proceed. Typically, the values of the calculated density and the measured density are desired to be within about 5% of each other to be considered sufficiently accurate. If the difference between the calculated density and the measured density are sufficiently accurate, then in step 470 the density for all fractions, including the C30+ fraction is calculated. Alternatively, if the difference between the calculated density and the measured density are not sufficiently accurate, (i.e., the difference between the calculated density and the measured density is greater than about 5%), then in step 480, another density value for the C30+ fraction is selected, and step 430 is repeated. The procedure is repeated until the difference between the calculated density and the measured density for the fluid is determined to be sufficiently accurate.

After the density of the C30+ fraction has been determined within sufficient accuracy, the C7+, C12+, and C20+ fraction densities can be determined as follows. For the determination of the C7+ fraction, the weights of all components from the C7 component up to and including the C30+ fraction are added together, and the sum is divided by 100 to obtain a total weight of the C7+ fraction. The volumes of each component from the C7 component up to and including the C30+ fraction are added together to obtain a total volume of the C7+ fraction. The total weight of the C7+ fraction is then divided by the total volume of the C7+ fraction to obtain a C7+ density.

Similarly, determination of the C12+ fraction proceeds as follows: the weights of all components from the C12 component up to and including the C30+ fraction are added together, and the sum is divided by 100 to obtain a total weight of the C12+ fraction. The volumes of each component from the C12 component up to and including the C30+ fraction are added together to obtain a total volume of the C12+ fraction. The total weight of the C12+ fraction is then divided by the total volume of the C12+ fraction to obtain a C7+ density.

The determination of the C20+ fraction proceeds as follows: the weights of all components from the C20 component up to and including the C30+ fraction are added together, and the sum is divided by 100 to obtain a total weight of the C20+ fraction. The volumes of each component from the C20 component up to and including the C30+ fraction are added together to obtain a total volume of the C20+ fraction. The total weight of the C20+ fraction is then divided by the total volume of the C20+ fraction to obtain a C20+ density.

In one embodiment of the present invention, a well bottom hydrocarbon sample is analyzed to determine total hydrocarbon composition. The hydrocarbon sample is heated to a temperature of at least about 200° F., preferably to a temperature of about 220° F., to produce the gas fraction and a liquid residue fraction, wherein the gas fraction includes carbon compounds up to about C6, dissolved gasses such as nitrogen, hydrogen sulfide and carbon dioxide, and trace amounts of C7 and C8 compounds. The number of moles of the liquid sample can be determined by dividing the measured mass of the liquid fraction by the measured molecular weight of the liquid fraction. Average molecular weight can be determined by freezing point depression. The number of moles of the gas sample can be determined, for example, by dividing the measured volume of gas fraction at standard conditions (60° F.) with the known volume of one mole of gas at standard conditions (23,690 cm$^3$). The total number of moles was determined, for example, by adding the number of moles of the liquid residue fraction and the number of moles of the gas fraction.

The number of moles of each individual component for both the liquid residue fraction and the gas fraction can then be determined, for example, by multiplying the mole fraction component determined by the gas chromatography, by the total number of moles of either liquid residue fraction or gas fraction. The sum of the individual moles of each of the gas and liquid residue fractions can then be calculated. The wellstream mole composition can then be determined, for example, by dividing the mole fraction of each component in the liquid residue fraction and the gas fraction by the total number of moles for both the liquid residue and the gas fractions. A mole percentage can then be determined from the calculation.

The gas chromatograph can produce a chromatogram that can include various different peaks corresponding to each individual component within the sample, based upon total retention time of the compound in the chromatograph. The areas for each individual peak correspond to the concentration of each individual compound present within an injected sample. Peak areas are typically automatically calculated by the gas chromatograph, and can be a main input into an associated computer program that can be utilized for determining the overall wellstream composition of a hydrocarbon sample.

For the liquid residue fraction, the molecular weight and density are specifically measured and are matched to determine the C30+ fraction component. In certain embodiments, in determining the C30+ fraction component of a sample, the program portion of the present invention can utilize historical wellstream data relating to the measured molecular weights and densities for reservoirs, as well as the published molecular weights and densities of single carbon number (SCN), for reliable determination of the C30+ fraction.

In certain embodiments of the present invention, the chromatograph can be calibrated prior to analyzing a wellstream hydrocarbon sample. For example, in certain instances, a reference standard containing a known amount of C30+ fraction is used to calibrate the gas chromatograph. For a light oil sample, the calibration reference sample can include between about 30% and 40% by weight of a known C30+ fraction, preferably up to about 35% by weight of a known $C_{30+}$ fraction. For a heavy oil sample, the calibration reference sample can include between about 40% and 50% by weight of a known C30+ fraction, preferably up to about 45% by weight of the known C30+ fraction. In certain embodiments, a known amount of a light hydrocarbon reference, for example hexane, can also be injected with the C30+ fraction reference sample, to concurrently determine average retention times for both hexane and the C30+ fraction sample. The response factor of the internal standard can be adjusted during quantification to match the final calculated C30+ fraction based upon the weight fraction of the C30+ fraction.

Calibration of the thermal conductivity and flame ionization detectors can be by known means, such as by using standard gas and liquid samples. For example, the thermal conductivity detector responses can be measured for various compounds, including nitrogen, carbon dioxide, and alkanes having between 1 and 9 carbon atoms, based upon the mass injected and the peak areas from the analysis of the standard samples.

Calibration of the flame ionization detector can be done using known standards, or a separate standard can be prepared for such a calibration. For example, in certain embodiments of the present invention, a liquid mixture that includes a known concentration of hydrocarbons having between about 5 and 16 carbon atoms can be prepared by measuring between about 0.05 and 0.40 mg of the various hydrocarbons and placing into a clean, dry volumetric flask, which after all of the paraffinic hydrocarbons were added, can be topped to volume with pentane. Density of the calibration sample can be calculated by comparing the empty mass of the flask, and the mass of the flask with the liquid samples placed therein.

The improved analysis methods of the present invention provide data for accurate compositional simulations, estimation of reserves, field surveillance of enhanced oil recovery, and gas cycling projects. In addition, providing accurate compositional data is essential to the tuning of equation of state fluid characterization models for input into reservoir and process simulations. The technique presented in this paper has been successfully used to acquire an extended wellstream composition of oil and gas samples and it has several advantages over the traditional method of compositional analysis.

The method of the present invention offers multiple advantages over prior art methods for acquiring fluid composition data. For example, in contrast to many of the prior art methods, which only provide compositional analysis only up to a C12+ fraction, certain embodiments of the present invention can provide extended compositional data up to a C30+ fraction, along with various other plus fraction properties. In other embodiments, the methods according to the present invention include flashing the sample at atmospheric conditions by heating the hydrocarbon or wellstream oil sample up to about 220° F., rather than heating the vessel to temperatures greater than about 500° F., or even above about 600° F., as required by the prior art. In addition to requiring additional energy and equipment, heating the sample being analyzed to the higher temperatures can result in partial cracking of the fluid sample, thereby providing an inaccurate determination of the composition of the sample. The recovered gas and liquid fractions from the flashing of the hydrocarbon sample, according to the present invention, can be analyzed using gas chromatography, and the resulting compositional analysis can then be imported into a computer program designed for accurate quantification of the analysis. The measured volumes of the various fractions and the measured molecular weight and density of the liquid residue fraction can then be utilized and applied to compute a well-stream composition for the fluid. Thus, in certain embodiments of the present invention, the use of the present methods can result in the saving of significant time, and can increase and in certain instances, double the number of fluids analyses that can be performed each year.

The $C_{30+}$ fraction data is preferred to be used over C12+ or C20+ fractional data for simulations or equation of state calculations. Accurate knowledge of each component up to the C30+ fraction, rather than a lower fraction, improves accuracy of simulations and reduces the number of corrections or adjustments that must be made.

EXAMPLES

The examples below show calibration and usage of at least one embodiment of the present inventive methods for the compositional analysis of a fluid.

Prior to analyzing either a bottom-hole sample or a fraction obtained from a sample from a liquid separator, precautions were taken to ensure that the sample was in a single phase by pressurizing and homogenizing the sample to a pressure above the bubble point through use of a Sprague pump connected to the hydraulic side of the sample cylinder. The sampling end of the cylinder was connected to the receiving end of the still, which in turn was connected through the still outlet to the inlet of the topping cylinders. When all connections were completed between the cylinders, the system was evacuated through the topping unit to the sample end of the cylinder. The sample end valve was then opened slightly, thereby ensuring that the sample pressure was maintained at a pressure that was above the bubble point pressure. Between about 50 and 100 mL of sample, depending on the nature of the fluid sample, were flash heated at room temperature conditions. For example, the fluid sample was heated to a temperature of about 220° F., and the evolved gas was collected and measured at the topping unit. Additionally, the collected gas sample was analyzed by gas chromatography and also measured to determine the volume of the collected gas sample. In a similar fashion, liquid residue was cooled and collected for gas chromatographic analysis, and the density and molecular weight were also measured.

The methods of the present invention were applied to several oil and gas reservoir fluids in Saudi Arabia, and were tested on various fluids from the oil and gas reservoirs that cover a range of API gravities. Table 1 provides an exemplary calibration for a natural gas analyzer. The calibration results demonstrate good reproducibility with the composition of the standard up to the C9 hydrocarbon components, with particular accuracy being shown light compounds up to and including the C5 hydrocarbon components.

TABLE 1

Result of Natural Gas Analyzer Calibration.

| Component | Calibration Composition (mol %) (Standard Mixture) | Composition (mol %) (GC) |
|---|---|---|
| $N_2$ | 9.87 | 10.04 |
| $CO_2$ | 2.05 | 2.06 |
| $H_2S$ | 3.07 | 3.02 |
| C1 | 65.60 | 65.53 |
| C2 | 8.02 | 8.01 |
| C3 | 6.09 | 6.00 |
| i-C4 | 1.02 | 1.00 |
| n-C4 | 2.00 | 1.99 |
| i-C5 | 0.48 | 0.50 |
| n-C5 | 0.93 | 1.01 |
| C6 | 0.46 | 0.50 |
| C7 | 0.17 | 0.19 |
| C8 | 0.20 | 0.10 |
| C9 | 0.05 | 0.05 |
| Total | 100.00 | 100.00 |

Analysis of the calibration gas sample show good accuracy by gas chromatography for the majority of the components of the calibration composition correlating well by gas chromatographic analysis. Similarly, Table 2 provides an exemplary calibration for gas chromatographic analysis of a liquid sample. The comparison shows good reproducibility of the composition of the sample as compared with the standard mixture. The liquid calibration sample includes hydrocarbons ranging from C5 and C16.

TABLE 2

Condensate GC Calibration with Liquid Mixture.

| Component | Calibration Composition (mol %) (Standard Mixture) | Composition (mol %) (GC) |
|---|---|---|
| C5 | 11.44 | 11.72 |
| C6 | 12.18 | 12.60 |
| C7 | 11.67 | 11.70 |
| C8 | 9.85 | 9.79 |
| C9 | 8.23 | 8.18 |
| C10 | 8.16 | 7.42 |

TABLE 2-continued

Condensate GC Calibration with Liquid Mixture.

| Component | Calibration Composition (mol %) (Standard Mixture) | Composition (mol %) (GC) |
|---|---|---|
| C11 | 7.03 | 7.11 |
| C12 | 13.25 | 13.23 |
| C16 | 18.19 | 18.25 |
| Total | 100.00 | 100.00 |

Tables 3 and 4 show the results of ASTM D2887 reference gas oil for the condensate and oil gas chromatographs. Table 3 shows the calibration results. For example, the calibration sample included approximately 3% by weight of the C30+ fraction, and corresponds well to the measured composition of about 3.07% by weight of the C30+ fraction. With respect to Table 4, the calibration sample included approximately 35% by weight of the C30+ fraction, and corresponds well to the measured composition of about 35.17% by weight of the C30+ fraction.

TABLE 3

Condensate Gas Chromatograph Calibration with Gas Oil Reference Mixture.

| Component | Calibration Composition (wt %) |
|---|---|
| C1 | 0.00 |
| C2 | 0.00 |
| C3 | 0.00 |
| i-C4 | 0.00 |
| n-C4 | 0.00 |
| i-C5 | 0.00 |
| n-C5 | 0.00 |
| C6 | 0.02 |
| C7 | 0.21 |
| C8 | 1.95 |
| C9 | 3.41 |
| C10 | 4.00 |
| C11 | 3.64 |
| C12 | 3.60 |
| C13 | 4.42 |
| C14 | 4.56 |
| C15 | 5.10 |
| C16 | 5.21 |
| C17 | 5.99 |
| C18 | 7.24 |
| C19 | 7.77 |
| C20 | 6.90 |
| C21 | 5.77 |
| C22 | 5.23 |
| C23 | 4.81 |
| C24 | 4.32 |
| C25 | 4.07 |
| C26 | 2.64 |
| C27 | 2.56 |
| C28 | 2.02 |
| C29 | 1.48 |
| C30+ | 3.07 |
| Total | 100.00 |

TABLE 4

Oil GC Calibration with Gas Oil Reference Mixture.

| Component | Composition (wt. %) |
|---|---|
| C1 | 0.00 |
| C2 | 0.00 |
| C3 | 0.02 |
| i-C4 | 0.03 |
| n-C4 | 0.13 |
| i-C5 | 0.16 |
| n-C5 | 0.27 |
| C6 | 0.79 |
| C7 | 2.08 |
| C8 | 2.89 |
| C9 | 2.84 |
| C10 | 2.94 |
| C11 | 2.80 |
| C12 | 3.03 |
| C13 | 3.43 |
| C14 | 3.18 |
| C15 | 3.70 |
| C16 | 3.31 |
| C17 | 3.19 |
| C18 | 3.17 |
| C19 | 3.13 |
| C20 | 2.93 |
| C21 | 2.79 |
| C22 | 2.61 |
| C23 | 2.54 |
| C24 | 2.30 |
| C25 | 2.21 |
| C26 | 2.18 |
| C27 | 2.15 |
| C28 | 1.98 |
| C29 | 2.05 |
| C30+ | 35.17 |
| Total | 100.00 |

Table 5 shows calibration data for a liquid hydrocarbon sample for the oil gas chromatograph. Comparisons of the mole percent of the prepared sample and the measured values as determined by the gas chromatograph show good results.

TABLE 5

Oil GC Calibration with Liquid Mixture.

| Component | Composition (mol %) (Standard Mixture) | Composition (mol %) (GC) |
|---|---|---|
| C5 | 13.01 | 12.65 |
| C6 | 11.98 | 11.66 |
| C7 | 9.95 | 9.99 |
| C8 | 9.85 | 9.98 |
| C9 | 7.98 | 8.04 |
| C10 | 8.11 | 8.05 |
| C11 | 7.57 | 7.55 |
| C12 | 7.01 | 7.07 |
| C16 | 24.54 | 25.01 |
| Total | 100.00 | 100.00 |

Tables 6-8 provide the results of the analysis of various well samples taken from reservoirs in Saudi Arabia. Samples were analyzed using the techniques described herein, wherein the liquid sample is heated to a temperature of about 220° F. to produce a liquid and a gas fraction, and each fraction was subsequently analyzed by gas chromatography. Results of the analyzed gas compositions and the liquid compositions were mathematically recombined using a computer program. A gas chromatogram that includes the total area of the gas and the liquid fractions was directly loaded into the computer program. The weight of the liquid sample and the measured density of the stock tank oil were also entered into the program. In addition, the pressure and temperature during the flash heating were recorded by a manometer and a thermocouple, respectively, which were coupled to the topping unit. Finally, the total volume of gas measured at the topping unit (at the flashed temperature and pressure) was measured and entered into the computer program.

After all of the data was entered into the computer program, the plus fraction molecular weight and density were matched to the measured molecular weight and density to obtain the $C_{30+}$ molecular weight and density. After the C30+ molecular weight and density were calculated, other plus fractions properties such as C7+, C12+, C20+ propertied were back calculated. Tables 6A-8B provide extended composition results up to a C30+ fraction, and the plus fraction properties of producing black oil, volatile oil and gas condensate in Saudi Arabia. The well stream composition was calculated using methods according to an embodiment of the present invention. The compositional analysis of a well stream determined utilizing conventional methods are provided in Table 9. The molecular compositions were found to be similar, however there is noticeable variation in the amount of heptanes plus and the dodecanes plus fractions, most likely because of the increased temperature the fluids were subjected to in the conventional method. Accurate determination and the availability of extended fluid composition of reservoir fluids is critical, not only to characterize and produce the reservoir, but also to design well completions and process systems.

Table 6A shows a black oil sample. The table provides the results of the gas and liquid fractions, and shows the combined total well-stream composition. Table 6B shows individual properties of the well-stream composition. Similar results are shown in Tables 7A and 7B for a volatile oil sample and in Tables 8A and 8B for a gas condensate sample.

TABLE 6A

Composition of Well-XXX. Black Oil.

| Component | MW (g/mol) | GC Gas wt % | GC Gas mole % | GC Oil wt % | GC Oil mole % | Well-Stream wt % | Well-Stream mole % |
|---|---|---|---|---|---|---|---|
| $N_2$ | 28.01 | 1.06 | 1.49 | 0.00 | 0.00 | 0.07 | 0.46 |
| $CO_2$ | 44.01 | 9.32 | 8.33 | 0.00 | 0.00 | 0.63 | 2.56 |
| $H_2S$ | 34.08 | 13.40 | 15.47 | 0.00 | 0.00 | 0.91 | 4.76 |
| C1 | 16.04 | 8.88 | 21.79 | 0.00 | 0.00 | 0.60 | 6.71 |
| C2 | 30.07 | 10.48 | 13.71 | 0.00 | 0.04 | 0.72 | 4.25 |
| C3 | 44.10 | 19.24 | 17.17 | 0.05 | 0.28 | 1.36 | 5.48 |
| i-C4 | 58.12 | 3.53 | 2.39 | 0.03 | 0.13 | 0.27 | 0.83 |
| n-C4 | 58.12 | 13.75 | 9.31 | 0.23 | 0.94 | 1.15 | 3.52 |
| i-C5 | 72.15 | 4.90 | 2.67 | 0.28 | 0.94 | 0.60 | 1.47 |
| n-C5 | 72.15 | 7.57 | 4.13 | 0.64 | 2.13 | 1.11 | 2.75 |
| C6 | 84.00 | 6.04 | 2.83 | 1.92 | 5.47 | 2.20 | 4.66 |
| C7 | 100.21 | 1.53 | 0.60 | 2.67 | 6.40 | 2.60 | 4.61 |
| C8 | 107.00 | 0.27 | 0.10 | 3.21 | 7.20 | 3.01 | 5.02 |
| C9 | 121.00 | 0.03 | 0.01 | 3.54 | 7.02 | 3.30 | 4.86 |
| C10 | 134.00 | 0.00 | 0.00 | 3.66 | 6.55 | 3.41 | 4.53 |
| C11 | 147.00 | 0.00 | 0.00 | 3.57 | 5.82 | 3.33 | 4.03 |
| C12 | 161.00 | 0.00 | 0.00 | 3.39 | 5.04 | 3.16 | 3.49 |
| C13 | 175.00 | 0.00 | 0.00 | 3.36 | 4.61 | 3.13 | 3.19 |
| C14 | 190.00 | 0.00 | 0.00 | 3.14 | 3.96 | 2.92 | 2.74 |
| C15 | 206.00 | 0.00 | 0.00 | 3.24 | 3.78 | 3.02 | 2.61 |
| C16 | 222.00 | 0.00 | 0.00 | 3.23 | 3.49 | 3.01 | 2.41 |
| C17 | 237.00 | 0.00 | 0.00 | 2.78 | 2.81 | 2.59 | 1.95 |
| C18 | 251.00 | 0.00 | 0.00 | 2.74 | 2.62 | 2.55 | 1.81 |
| C19 | 263.00 | 0.00 | 0.00 | 2.85 | 2.60 | 2.65 | 1.80 |
| C20 | 275.00 | 0.00 | 0.00 | 2.66 | 2.32 | 2.48 | 1.61 |
| C21 | 291.00 | 0.00 | 0.00 | 2.63 | 2.17 | 2.45 | 1.50 |
| C22 | 300.00 | 0.00 | 0.00 | 2.43 | 1.95 | 2.27 | 1.35 |
| C23 | 312.00 | 0.00 | 0.00 | 2.41 | 1.86 | 2.25 | 1.28 |
| C24 | 324.00 | 0.00 | 0.00 | 2.20 | 1.63 | 2.05 | 1.13 |
| C25 | 337.00 | 0.00 | 0.00 | 2.21 | 1.57 | 2.06 | 1.09 |
| C26 | 349.00 | 0.00 | 0.00 | 2.00 | 1.37 | 1.86 | 0.95 |
| C27 | 360.00 | 0.00 | 0.00 | 2.11 | 1.41 | 1.97 | 0.97 |
| C28 | 372.00 | 0.00 | 0.00 | 2.14 | 1.38 | 1.99 | 0.95 |

TABLE 6A-continued

Composition of Well-XXX. Black Oil.

| Component | MW (g/mol) | GC Gas wt % | GC Gas mole % | GC Oil wt % | GC Oil mole % | Well-Stream wt % | Well-Stream mole % |
|---|---|---|---|---|---|---|---|
| C29 | 382.00 | 0.00 | 0.00 | 2.30 | 1.45 | 2.15 | 1.00 |
| C30+ | 700.00 | 0.00 | 0.00 | 32.35 | 11.08 | 30.15 | 7.67 |
| AVG MW | | | 39.35 | | 239.78 | | 178.09 |
| Total Mole % | | | 100 | | 100 | | 100 |

TABLE 6B

Properties of Well-XXX. Black Oil.

Single Stage Flash Data

| | Original STO |
|---|---|
| GOR (SCF/STB) | 219 |
| STO Density (g/cc) | 0.8864 |
| STO API Gravity | 28.1 |

| Properties | Flashed Gas | Flashed Oil | Well-Stream |
|---|---|---|---|
| Mole % | | | |
| C7+ | 0.71 | 90.07 | 62.56 |
| C12+ | 0.00 | 57.08 | 39.51 |
| C20+ | 0.00 | 28.18 | 19.51 |
| C30+ | 0.00 | 11.08 | 7.67 |
| Mass % | | | |
| C7+ | 1.83 | 96.84 | 90.38 |
| C12+ | 0.00 | 80.18 | 74.73 |
| C20+ | 0.00 | 55.46 | 51.69 |
| C30+ | 0.00 | 32.35 | 30.15 |
| Molar Mass | | | |
| C7+ | 101.45 | 257.83 | 257.28 |
| C12+ | | 336.87 | 336.87 |
| C20+ | | 471.91 | 471.91 |
| C30+ | | 700.00 | 700.00 |
| Density (g/cc) | | | |
| C7+ | 0.7299 | 0.8835 | 0.8832 |
| C12+ | | 0.9126 | 0.9126 |
| C20+ | | 0.9505 | 0.9505 |
| C30+ | | 0.9990 | 0.9990 |
| Fluid Density at STP Condition (g/cc) | | 0.8864 | |
| Gas Gravity (Air = 1) | 1.3588 | | |
| Dry Gross Heating Content (BTU/scf) | 1825.3 | | |
| Wet Gross Heating Content (BTU/scf) | 1793.4 | | |

Tables 7A and 7B show similar results for the analysis of a volatile oil sample according to the methods described herein.

TABLE 7A

Composition of Well-XXXX. Volatile Oil.

| Component | MW (g/mol) | Separator Gas wt % | Separator Gas mole % | Separator Oil wt % | Separator Oil mole % | Well-Stream wt % | Well-Stream mole % |
|---|---|---|---|---|---|---|---|
| $N_2$ | 28.01 | 6.03 | 5.17 | 0.02 | 0.10 | 0.82 | 2.37 |
| $CO_2$ | 44.01 | 0.38 | 0.21 | 0.01 | 0.02 | 0.06 | 0.11 |
| $H_2S$ | 34.08 | 0.00 | 0.00 | 0.00 | 0.00 | 0.00 | 0.00 |
| C1 | 16.04 | 41.36 | 61.91 | 0.46 | 3.57 | 5.89 | 30.03 |
| C2 | 30.07 | 25.08 | 20.03 | 1.58 | 6.58 | 4.70 | 13.24 |

TABLE 7A-continued

Composition of Well-XXXX. Volatile Oil.

| Component | MW (g/mol) | Separator Gas wt % | Separator Gas mole % | Separator Oil wt % | Separator Oil mole % | Well-Stream wt % | Well-Stream mole % |
|---|---|---|---|---|---|---|---|
| C3 | 44.10 | 15.07 | 8.20 | 2.90 | 8.25 | 4.52 | 9.03 |
| i-C4 | 58.12 | 3.02 | 1.25 | 1.14 | 2.47 | 1.39 | 2.16 |
| n-C4 | 58.12 | 4.57 | 1.89 | 2.22 | 4.79 | 2.53 | 3.96 |
| i-C5 | 72.15 | 1.38 | 0.46 | 1.06 | 1.84 | 1.10 | 1.38 |
| n-C5 | 72.15 | 1.20 | 0.40 | 1.12 | 1.94 | 1.13 | 1.38 |
| C6 | 84.00 | 1.05 | 0.30 | 3.12 | 4.65 | 2.84 | 2.66 |
| C7 | 100.21 | 0.42 | 0.10 | 6.41 | 8.02 | 5.61 | 4.18 |
| C8 | 107.00 | 0.09 | 0.02 | 9.99 | 11.71 | 8.68 | 5.99 |
| C9 | 121.00 | 0.35 | 0.07 | 8.51 | 8.82 | 7.43 | 4.48 |
| C10 | 134.00 | 0.00 | 0.00 | 7.65 | 7.16 | 6.64 | 3.55 |
| C11 | 147.00 | 0.00 | 0.00 | 5.84 | 4.98 | 5.06 | 2.55 |
| C12 | 161.00 | 0.00 | 0.00 | 5.02 | 3.91 | 4.35 | 2.17 |
| C13 | 175.00 | 0.00 | 0.00 | 5.02 | 3.60 | 4.36 | 1.50 |
| C14 | 190.00 | 0.00 | 0.00 | 4.02 | 2.65 | 3.48 | 1.27 |
| C15 | 206.00 | 0.00 | 0.00 | 3.80 | 2.31 | 3.29 | 1.08 |
| C16 | 222.00 | 0.00 | 0.00 | 2.87 | 1.62 | 2.49 | 0.80 |
| C17 | 237.00 | 0.00 | 0.00 | 2.72 | 1.44 | 2.36 | 0.80 |
| C18 | 251.00 | 0.00 | 0.00 | 2.82 | 1.41 | 2.45 | 0.78 |
| C19 | 263.00 | 0.00 | 0.00 | 2.58 | 1.23 | 2.24 | 0.68 |
| C20 | 275.00 | 0.00 | 0.00 | 2.15 | 0.98 | 1.86 | 0.54 |
| C21 | 291.00 | 0.00 | 0.00 | 1.93 | 0.83 | 1.67 | 0.46 |
| C22 | 300.00 | 0.00 | 0.00 | 1.67 | 0.70 | 1.45 | 0.39 |
| C23 | 312.00 | 0.00 | 0.00 | 1.54 | 0.62 | 1.34 | 0.34 |
| C24 | 324.00 | 0.00 | 0.00 | 1.45 | 0.56 | 1.25 | 0.31 |
| C25 | 337.00 | 0.00 | 0.00 | 1.37 | 0.51 | 1.19 | 0.28 |
| C26 | 349.00 | 0.00 | 0.00 | 1.86 | 0.67 | 1.62 | 0.37 |
| C27 | 360.00 | 0.00 | 0.00 | 1.09 | 0.38 | 0.95 | 0.21 |
| C28 | 372.00 | 0.00 | 0.00 | 1.69 | 0.57 | 1.47 | 0.29 |
| C29 | 382.00 | 0.00 | 0.00 | 1.55 | 0.51 | 1.35 | 0.28 |
| C30+ | 580.00 | 0.00 | 0.00 | 2.82 | 0.61 | 2.45 | 0.34 |
| AVG MW | | 24.01 | | 125.38 | | 80.34 | |
| Total Mole % | | 100 | | 100 | | 100 | |

TABLE 7B

Properties of Well-XXXX. Volatile Oil.

Single Stage Flash Data

| | Original STO |
|---|---|
| GOR (SCF/STB) | 638 |
| STO Density (g/cc) | 0.774 |
| STO API Gravity | 51.3 |

| Properties | Separator Gas | Separator Oil | Well-Stream |
|---|---|---|---|
| Mole % | | | |
| C7+ | 0.19 | 65.79 | 36.64 |
| C12+ | 0.00 | 25.11 | 13.95 |
| C20+ | 0.00 | 6.94 | 3.86 |
| C30+ | 0.00 | 0.61 | 0.34 |
| Mass % | | | |
| C7+ | 0.86 | 86.38 | 75.02 |
| C12+ | 0.00 | 47.98 | 41.61 |
| C20+ | 0.00 | 19.13 | 16.59 |
| C30+ | 0.00 | 2.82 | 2.45 |
| Molar Mass | | | |
| C7+ | 108.58 | 160.02 | 159.48 |
| C12+ | | 230.44 | 230.44 |
| C20+ | | 345.69 | 345.69 |
| C30+ | | 580.00 | 580.00 |

TABLE 7B-continued

Properties of Well-XXXX. Volatile Oil.

| Density (g/cc) | | | |
|---|---|---|---|
| C7+ | 0.7454 | 0.7957 | 0.7888 |
| C12+ | | 0.8246 | 0.8246 |
| C20+ | | 0.8838 | 0.8838 |
| C30+ | | 0.9020 | 0.9020 |
| Fluid Density at STP Condition (g/cc) | | 0.7740 | |
| Gas Gravity (Air = 1) | 0.8292 | | |
| Dry Gross Heating Content (BTU/scf) | 1351.3 | | |
| Wet Gross Heating Content (BTU/scf) | 1327.8 | | |

Tables 8A and 8B show similar results for the analysis of a gas condensate sample according to the methods described herein.

TABLE 8A

Composition of Well-XXXXX. Gas Condensate.

| Component | MW (g/mol) | Separator Gas wt % | Separator Gas mole % | Separator Oil wt % | Separator Oil mole % | Well-Stream wt % | Well-Stream mole % |
|---|---|---|---|---|---|---|---|
| N2 | 28.01 | 4.49 | 3.31 | 0.08 | 0.26 | 4.04 | 3.23 |
| CO2 | 44.01 | 7.19 | 3.37 | 0.67 | 1.42 | 6.52 | 3.32 |
| H2S | 34.08 | 0.00 | 0.00 | 0.00 | 0.00 | 0.00 | 0.00 |
| C1 | 16.04 | 61.78 | 79.48 | 3.29 | 19.15 | 55.76 | 77.99 |
| C2 | 30.07 | 12.56 | 8.62 | 2.31 | 7.17 | 11.50 | 8.58 |
| C3 | 44.10 | 6.05 | 2.83 | 2.58 | 5.46 | 5.69 | 2.89 |
| i-C4 | 58.12 | 1.49 | 0.53 | 1.07 | 1.72 | 1.45 | 0.56 |
| n-C4 | 58.12 | 2.22 | 0.79 | 2.04 | 3.28 | 2.21 | 0.85 |
| i-C5 | 72.15 | 1.08 | 0.31 | 1.64 | 2.12 | 1.14 | 0.35 |
| n-C5 | 72.15 | 0.87 | 0.25 | 1.52 | 1.97 | 0.94 | 0.29 |
| C6 | 84.00 | 1.22 | 0.30 | 4.62 | 5.14 | 1.57 | 0.42 |
| C7 | 100.21 | 0.73 | 0.15 | 8.19 | 7.63 | 1.50 | 0.33 |
| C8 | 107.00 | 0.26 | 0.05 | 13.01 | 11.36 | 1.57 | 0.33 |
| C9 | 121.00 | 0.06 | 0.01 | 10.79 | 8.33 | 1.16 | 0.22 |
| C10 | 134.00 | 0.00 | 0.00 | 9.03 | 6.30 | 0.93 | 0.16 |
| C11 | 147.00 | 0.00 | 0.00 | 6.60 | 4.19 | 0.68 | 0.10 |
| C12 | 161.00 | 0.00 | 0.00 | 5.58 | 3.24 | 0.57 | 0.08 |
| C13 | 175.00 | 0.00 | 0.00 | 5.08 | 2.71 | 0.52 | 0.07 |
| C14 | 190.00 | 0.00 | 0.00 | 3.91 | 1.92 | 0.40 | 0.05 |
| C15 | 206.00 | 0.00 | 0.00 | 3.38 | 1.53 | 0.35 | 0.04 |
| C16 | 222.00 | 0.00 | 0.00 | 2.65 | 1.12 | 0.27 | 0.03 |
| C17 | 237.00 | 0.00 | 0.00 | 2.05 | 0.81 | 0.21 | 0.02 |
| C18 | 251.00 | 0.00 | 0.00 | 1.93 | 0.72 | 0.20 | 0.02 |
| C19 | 263.00 | 0.00 | 0.00 | 1.65 | 0.59 | 0.17 | 0.01 |
| C20 | 275.00 | 0.00 | 0.00 | 1.29 | 0.44 | 0.13 | 0.01 |
| C21 | 291.00 | 0.00 | 0.00 | 1.02 | 0.33 | 0.11 | 0.01 |
| C22 | 300.00 | 0.00 | 0.00 | 0.83 | 0.26 | 0.09 | 0.01 |
| C23 | 312.00 | 0.00 | 0.00 | 0.67 | 0.20 | 0.07 | 0.00 |
| C24 | 324.00 | 0.00 | 0.00 | 0.52 | 0.15 | 0.05 | 0.00 |
| C25 | 337.00 | 0.00 | 0.00 | 0.43 | 0.12 | 0.04 | 0.00 |
| C26 | 349.00 | 0.00 | 0.00 | 0.37 | 0.10 | 0.04 | 0.00 |
| C27 | 360.00 | 0.00 | 0.00 | 0.31 | 0.08 | 0.03 | 0.00 |
| C28 | 372.00 | 0.00 | 0.00 | 0.24 | 0.06 | 0.02 | 0.00 |
| C29 | 382.00 | 0.00 | 0.00 | 0.16 | 0.04 | 0.02 | 0.00 |
| C30+ | 580.00 | 0.00 | 0.00 | 0.48 | 0.08 | 0.05 | 0.00 |
| AVG MW | | 20.64 | | 93.41 | | 22.44 | |
| Total Mole % | | 100 | | 100 | | | |

TABLE 8B

Properties of Well-XXXXX. Gas Condensate.

Single Stage Flash Data

|  | Original STO |
|---|---|
| GOR (SCF/STB) | 36355 |
| STO Density (g/cc) | 0.780 |
| STO API Gravity | 49.6 |

| Properties | Separator Gas | Separator Oil | Well-Stream |
|---|---|---|---|
| Mole % | | | |
| C7+ | 0.21 | 52.30 | 1.50 |
| C12+ | 0.00 | 14.48 | 0.36 |
| C20+ | 0.00 | 1.85 | 0.05 |
| C30+ | 0.00 | 0.08 | 0.00 |
| Mass % | | | |
| C7+ | 1.05 | 80.18 | 9.18 |
| C12+ | 0.00 | 32.56 | 3.35 |
| C20+ | 0.00 | 6.32 | 0.65 |
| C30+ | 0.00 | 0.48 | 0.05 |
| Molar Mass | | | |
| C7+ | 102.81 | 160.10 | 158.37 |
| C12+ |  | 237.00 | 237.00 |

TABLE 8B-continued

Properties of Well-XXXXX. Gas Condensate.

| | | | |
|---|---|---|---|
| C20+ | | 319.11 | 319.11 |
| C30+ | | 580.00 | 580.00 |
| Density (g/cc) | | | |
| C7+ | 0.7336 | 0.7958 | 0.7803 |
| C12+ | | 0.8295 | 0.8295 |
| C20+ | | 0.8770 | 0.8770 |
| C30+ | | 0.9020 | 0.9020 |
| Fluid Density at STP Condition (g/cc) | | 0.7800 | |
| Gas Gravity (Air = 1) | 0.7127 | | |

Table 9 shows a comparison of the compositions of the various well-samples provided in Tables 6-8, which provide compositional data up to and including a C30+ fraction, and compare the results utilizing a method according to one embodiment of the present invention, which utilizes temperatures up to about 220° F., against a comparative technique that utilizes high temperatures (i.e., about 550° F.) and distillation apparatus, and which only provides compositional data up to the C12+ fraction. As shown in Tables 6-8, the present technique provides compositional data for up to a C30+ fraction. This information regarding the heavier hydrocarbons present in a well-stream sample, provide for improved simulations of reservoirs.

TABLE 9

Comparison of the Compositions of the Comparative Analysis and Present Invention.

| Type | | Black Oil Well-XXX | | | Volatile Oil Well-XXXX | | | Gas Cond. Well-XXXXX | | |
|---|---|---|---|---|---|---|---|---|---|---|
| Well No. | | | | | | | | | | |
| Temp., °F. | | 550° F. | 220° F. | Err. % | 550° F. | 220° F. | Err. % | 550° F. | 220° F. | Err. % |
| Fluid | $N_2$ | 0.47 | 0.46 | 2.4 | 2.33 | 2.37 | 1.7 | 3.25 | 3.23 | 0.5 |
| Comp. | $CO_2$ | 2.58 | 2.56 | 0.6 | 0.11 | 0.11 | 0.0 | 3.32 | 3.32 | 0.1 |
| | $H_2S$ | 4.88 | 4.76 | 2.4 | 0.00 | 0.00 | 0.0 | 0.00 | 0.00 | 0.0 |
| | C1 | 6.68 | 6.71 | 0.4 | 29.49 | 30.03 | 1.8 | 77.98 | 77.99 | 0.0 |
| | C2 | 4.15 | 4.25 | 2.3 | 13.07 | 13.24 | 1.3 | 8.58 | 8.58 | 0.1 |
| | C3 | 5.51 | 5.48 | 0.6 | 8.97 | 9.03 | 0.7 | 2.90 | 2.89 | 0.2 |
| | i-C4 | 0.87 | 0.83 | 4.8 | 2.15 | 2.16 | 0.5 | 0.56 | 0.56 | 0.1 |
| | n-C4 | 3.49 | 3.52 | 0.8 | 3.95 | 3.96 | 0.3 | 0.86 | 0.85 | 1.0 |
| | i-C5 | 1.38 | 1.47 | 6.7 | 1.38 | 1.38 | 0.0 | 0.37 | 0.35 | 4.1 |
| | n-C5 | 2.70 | 2.75 | 1.7 | 1.39 | 1.38 | 0.7 | 0.30 | 0.29 | 2.5 |
| | C6 | 4.69 | 4.66 | 0.7 | 2.68 | 2.66 | 0.7 | 0.42 | 0.42 | 0.1 |
| | C7 | 4.63 | 4.61 | 0.3 | 4.24 | 4.18 | 1.4 | 0.34 | 0.33 | 1.5 |
| | C8 | 5.12 | 5.02 | 2.0 | 6.07 | 5.99 | 1.3 | 0.31 | 0.33 | 6.2 |
| | C9 | 4.91 | 4.86 | 1.0 | 4.56 | 4.48 | 1.8 | 0.22 | 0.22 | 2.1 |
| | C10 | 4.60 | 4.53 | 1.5 | 3.70 | 3.55 | 4.1 | 0.16 | 0.16 | 2.8 |
| | C11 | 4.10 | 4.03 | 1.7 | 2.57 | 2.55 | 0.8 | 0.11 | 0.10 | 5.8 |
| | C12+ | 39.24 | 39.51 | 0.7 | 13.34 | 12.93 | 3.1 | 0.32 | 0.36 | 11.8 |
| | Total | 100.00 | 100.00 | | 100.0 | 100.0 | | 100.0 | 100.0 | |
| C12+ | Density | 0.9109 | 0.9126 | 0.2 | 0.8298 | 0.8246 | 0.6 | 0.8310 | 0.8295 | 0.2 |
| Prop. | API | 23.8 | 23.5 | 1.3 | 39.0 | 40.1 | 2.8 | 38.8 | 39.1 | 0.8 |
| | MW | 334 | 337 | 0.9 | 234 | 230 | 1.5 | 244 | 237 | 2.9 |
| C7+ | Density | 0.8848 | 0.8524 | | 0.7964 | 0.7888 | | 0.7964 | 0.7803 | |
| Prop. | API | 28.4 | 34.5 | | 46.2 | 47.9 | | 46.2 | 49.8 | |
| | MW | 263 | 254 | | 163 | 159 | | 163 | 158 | |

Table 9 shows a comparison for three different types of samples: a black oil sample (corresponding to Tables 6A and 6B), a volatile oil sample (corresponding to Tables 7A and 7B), and a gas condensate sample (corresponding to Tables 8A and 8B). Additionally, the error associated with the comparative technique relative to the present invention is provided. As seen, for the black oil sample, the compositional error was greater than 5% for only one component compound (the error associated with concentration of i-C5 was approximately 6.7%). The errors for the black oil sample were typically less than about 2%. For the volatile oil sample, the two techniques provided results that were much closer for lower hydrocarbons, typically less than or about 1.5%. An error of approximately 4.1% was noted for the C10 component and an error of approximately 3.1% was noted for the C12+ component. Finally, analysis of the gas condensate fraction generally showed good correlation for composition of hydrocarbons up to and including the C4 components. Multiple components showed errors of between 4% and 6% (e.g., i-C5, 4.1% error; C8, 6.2% error; and C11, 6.2% error), and the C12+ component shows an error of about 11.8%. Similarly, as shown in Table 9, the methods of the present invention show improved accuracy with respect to the physical properties of the C12+ fractions.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

That which is claimed is:

1. A method for analyzing a hydrocarbon sample, the method comprising the steps of:
    separating the hydrocarbon sample into a first and second fraction, wherein the first fraction comprises hydrocarbons having a boiling point less than about 220° F. and the second fraction comprises hydrocarbons having a boiling point greater than about 220° F.;
    measuring the volume of the first fraction;
    measuring the mass, density and molecular weight of the second fraction;
    determining the composition of the first fraction by gas chromatography with a first gas chromatograph;
    determining the composition of the second fraction by gas chromatography with a second gas chromatograph; and
    combining the compositions of the first and second fractions to obtain a total composition of the hydrocarbon sample up to a C30+ hydrocarbon fraction.

2. The method of claim 1, wherein the hydrocarbon sample is heated under atmospheric conditions to a temperature of between about 200° F. and 230° F.

3. The method of claim 1, wherein the hydrocarbon sample is heated under atmospheric conditions to a temperature of between about 220° F. and 225° F.

4. The method of claim 1, further comprising the step of determining the number of moles of the first fraction.

5. The method of claim 1, wherein the step of determining the molecular weight of the second fraction comprises the steps of:
    calculating the liquid mass of each fraction up to and including the C29 component;
    selecting an estimated molecular weight of the C30+ fraction;
    calculating the total molecular weight of the hydrocarbon sample from the estimated C30+ molecular weight; and
    confirming the estimated value of the molecular weight of the C30+ fraction.

6. The method of claim 1, wherein the step of determining the density of the second fraction comprises the steps of:
    estimating the density of the C30+ fraction;
    determining the total fluid density of the hydrocarbon sample utilizing the estimated density of the C30+ fraction; and
    confirming the total fluid density of the hydrocarbon sample.

7. The method of claim 1, further comprising determining the number of moles of the second fraction.

8. The method of claim 1, further comprising calibrating the first and second gas chromatographs prior to determining the composition of the first and second fractions.

9. A method for analyzing the hydrocarbon composition of a hydrocarbon bearing reservoir, the method comprising the steps of:
    obtaining a hydrocarbon sample from the hydrocarbon bearing reservoir;
    heating the hydrocarbon sample to produce two fractions, wherein the first fraction has an upper boiling point approximately less than or equal to the lower boiling point of the second fraction, wherein the upper boiling point of the first fraction is between about 200° F. and 250° F.;
    providing the first and second fractions to first and second gas chromatographs to obtain compositional analysis of the first and second fractions;
    determining the molecular weight and density for the first and second fractions; and
    combining the compositional analysis of the first fraction and the compositional analysis of the second fraction to obtain a total compositional analysis of the hydrocarbon sample.

10. The method of claim 9 wherein the upper boiling point of the first fraction is between about 200° F. and about 230° F.

11. The method of claim 9 further comprising the step of measuring the volume of the first and second fractions.

12. The method of claim 9 further comprising the step of determining the number of moles of the first and second fractions.

13. The method of claim 9, wherein the step of determining the molecular weight of the second fraction comprises the steps of:
    calculating the liquid mass of each fraction up to and including the C29 component;
    selecting an estimated molecular weight of the C30+ fraction and calculating the liquid mass of the C30+ fraction;

calculating the total molecular weight of the hydrocarbon sample from the estimated C30+ molecular weight; and confirming the estimated value of the molecular weight of the C30+ fraction.

14. The method of claim 9, wherein the step of determining the density of the second fraction comprises the steps of:

estimating the density of the C30+ fraction;

determining the total fluid density of the hydrocarbon sample utilizing the estimated density of the C30+ fraction; and confirming the total fluid density of the hydrocarbon sample.

* * * * *